(12) United States Patent
Gharda

(10) Patent No.: US 8,604,219 B2
(45) Date of Patent: Dec. 10, 2013

(54) METHOD FOR SYNTHESIS OF N-ALKYL CARBAZOLE AND DERIVATIVES THEREOF

(76) Inventor: Keki Hormusji Gharda, Mumbai (IN)

( * ) Notice: Subject to any disclaimer, the term of this patent is extended or adjusted under 35 U.S.C. 154(b) by 0 days.

(21) Appl. No.: 13/391,141

(22) PCT Filed: Jun. 10, 2010

(86) PCT No.: PCT/IN2010/000394
§ 371 (c)(1),
(2), (4) Date: Feb. 17, 2012

(87) PCT Pub. No.: WO2011/024186
PCT Pub. Date: Mar. 3, 2011

(65) Prior Publication Data
US 2012/0149915 A1    Jun. 14, 2012

(30) Foreign Application Priority Data
Aug. 24, 2009 (IN) .......................... 1941/MUM/2009

(51) Int. Cl.
*C07D 209/86* (2006.01)

(52) U.S. Cl.
USPC ..................................................... 548/447

(58) Field of Classification Search
None
See application file for complete search history.

(56) References Cited

U.S. PATENT DOCUMENTS

| | | | | |
|---|---|---|---|---|
| 1,494,879 A * | 5/1924 | Atack | ........................... | 548/447 |
| 1,662,061 A * | 3/1928 | Na | ................................ | 548/447 |
| 2,351,171 A * | 6/1944 | Weinmayr | .................... | 548/447 |
| 2,456,378 A * | 12/1948 | Cislak et al. | ................. | 548/447 |
| 2,481,292 A * | 9/1949 | Conover | ....................... | 548/447 |
| 2,921,942 A * | 1/1960 | Na | ................................ | 548/447 |
| 3,041,349 A * | 6/1962 | Bearse et al. | ................. | 548/420 |
| 4,957,609 A * | 9/1990 | Godfrey et al. | .......... | 204/157.71 |
| 5,393,894 A | 2/1995 | Becherer et al. | | |
| 5,856,516 A * | 1/1999 | Buysch et al. | ................ | 548/447 |
| 5,902,884 A * | 5/1999 | Bauer et al. | ................... | 548/447 |

FOREIGN PATENT DOCUMENTS

| | | |
|---|---|---|
| DE | 374098 | 4/1923 |
| DE | 2132961 | 1/1973 |
| DE | 3007196 A1 | 9/1980 |
| EP | 0104601 A1 | 8/2008 |

OTHER PUBLICATIONS

Chemical Abstracts, vol. 82. Abstract No. 45003 1975.
Yutaka Tsunashima, Masatane Kuroki. Journal of Heterocyclic Chemistry, vol. 18. 315 (1981). The chemistry of carbazole. VI. On the formation of N-ethylcarbazoles in the cadogan reaction.
BIOS Final Report 986, 197.
Lissel, M.; Schmidt, S.; Neumann, B. Synthesis 1986, 382-383. Use of Dimethyl Carbonate as a Methylation Agent under Phase Transfer-Catalyzed Conditions.
Trotta. F. et al. Journal of Organic Chemistry, vol. 52, 1300, 1987. Selective Mono-N-alkylation of Aromatic Amines by Dialkyl Carbonate under Gas-Liquid Phase-Transfer Catalysis (GL-PTC) Conditions.
Rogers and Corson, J. Am. Soc. 69, 2910, 1947. One-Step Synthesis of 1,2,3,4-Tetrahydrocarbazole and 1,2-Benzo-3,4-dihydrocarbazole.
Barclay and Campbell, J Chem. Soc.1945. 530. Dehydrogenation of Tetrahydrocarbazoles by Chloranil.
K. Darrell Berlin; Peter E. Clark, Jack Schroeder and Darrell Hopper, Proc. of the Okala. Acad. of sci. for 1966, 215-220. Synthesis of 1,2,3,4-Tetrahydrocarbazoles with Large Groups—Aromatization to Carbazoles.
E. Campaigne and R. D Lake, Journal of Organic Chemistry (1959), 24, 478-87. Synthesis of Tetrahydrocarbazoles and Carbazoles by the Bischler Reaction.
Lissel, M. Reactions with Dimetbyl Carbonate, 2-N-Methylation of Imidamle and Derivatives. Liebigs Annalen der Chemie 1987, 77-79.

\* cited by examiner

*Primary Examiner* — Nyeemah A Grazier

(57) ABSTRACT

Disclosed is a process for the preparation of N-alkyl carbazole. Said process comprises: a) chlorinating cyclohexanone to form 2-chlorocyclohexanone; b) reacting 2-chlorocyclohexanone with N-ethyl aniline to form 2-(N-ethyl anilino) cyclohexanone; c) cyclizing 2-(N-ethyl anilino) cyclohexanone by refluxing with simultaneous water removal to obtain 9-ethyltetrahydrocarbazole; d) treating 9-ethyl-tetrahydrocarbazole with concentrated hydrochloric acid followed by water wash for removing N-ethyl aniline; e) dehydrogenating 9-ethyltetrahydrocarbazole by heating 9-ethyltetrahydrocarbazole in a solvent, in presence of a catalyst to obtain N-alkyl carbazole.

14 Claims, No Drawings

METHOD FOR SYNTHESIS OF N-ALKYL CARBAZOLE AND DERIVATIVES THEREOF

The present application is the U.S. national phase application of PCT Application No. PCT/IN2010/000394, filed Jun. 10, 2010, which claims priority to Indian Patent Application No. 1941/MUM/2009, filed Aug. 24, 2009, the entirety of both of which are hereby incorporated by reference.

FIELD OF INVENTION

The present invention relates to a novel method for synthesis of N-alkyl carbazole and its derivatives.

BACKGROUND OF THE INVENTION

Carbazole and its derivatives, namely N-ethyl carbazole has wide application in the synthesis of dyes, pigments and insecticide. Carbazole derivatives are also used widely in electrical industry, high heat-resistant polymers, concrete plasticizers and the like. Carbazole is also one of the important constituents of coal tar. High temperature coal tar contains on an average 1.5% carbazole. Carbazole is also obtained as a co-product in the production of anthracene, both by physical separation (extraction with pyridine, ketone, N-methyl pyrrolidone (NMP), dimethylacetamide, dialkyl sulfoxide, dialkyl formamide) or chemical separation (by means of KOH, or concentrated $H_2SO_4$ fusion).

Plethora of published literature for the synthesis of chlorocyclohexanone from cyclohexanone is available. Aromatic primary and secondary amines are also available and can be made by reduction of corresponding nitro derivatives. N-ethylcarbazole is an important intermediate product for the preparation of valuable dyestuffs. It is prepared in the industries by reaction of carbazole with potassium hydroxide or potassium carbonate to give the potassium salt of carbazole, which is then ethylated with an ethyl halide or with diethyl sulphate (See DE-B2132961). Other processes for the preparation of N-ethylcarbazole from carbazole use, for example, ethyl benzenesulphonate (Chemical Abstracts, Volume 82, Abstract No. 45003 1975), diethyl N-(o-tolyl) phosphoramidate (*Journal of Heterocyclic Chemistry*, Volume 18, page 315 (1981)) or 1,1-diethoxyethylium tetrafluoborate, However, these process have no industrial importance.

All the known industrial preparation processes have the disadvantage that large amount of inorganic salts are produced which are to be removed from the process waste waters by evaporation of the waste water in a labour- and energy-intensive manner and then have to be dumped, or which finally enter rivers with the waste waters via clarification plants. These processes are environmentally unfriendly and produce large amount of solid and liquid waste. For example, if the process described in BIOS Final Report 986, page 197 is used, wastewater obtained comprises about 220 kg of potassium chloride per tonne of N-ethylcarbazole produced. By the process described in DE-B-2132961, about 490 kg of potassium sulphate is found in the waste water per tonne of N-ethylcarbazole. The processes in which ethyl halides are used as ethylating agents also have the further disadvantage that a very expensive purification of the waste air must be carried out to avoid emission of organic halogen compounds, since simple combustion of the waste air is not possible because of the halogen content. A content of organic halogen compounds in the wastewater also cannot be avoided in these processes with aqueous working-up of the reaction mixture. Furthermore, both the use of ethyl halides and that of diethyl sulphate require particular measures when handling these substances because of the toxic and carcinogenic properties. An improved process for the preparation of ethylcarbazole would therefore be extremely desirable for both the ecological and industrial hygiene reasons. Instead of alkyl halides or dialkyl sulphates, dialkyl carbonates can in some cases be employed in alkylation of amines; thus, for example, the use of dimethyl carbonate in the presence of phase transfer catalysts, such as crown ethers, instead of dimethyl sulphate for methylation of imidazole is described in Liebigs Annalen der Chemie 1987, page 77. This publication refers to the pronounced difference in reactivity between dimethyl carbonate and diethyl carbonate and in fact under no circumstances has a defined product has been obtained with diethyl carbonate. The different behavior of dimethyl and diethyl carbonate and the poor results achieved with the latter are also discussed, for example, in Synthesis 1986, page 382. Ethylations on the nitrogen atom of amide groups by means of diethyl carbonate are possible. European Patent Application EP-A-410214 mentions the reaction of urethanes with diethyl carbonate in the presence of at least equivalent amounts of alkali metal or alkaline earth metal carbonates and additional phase transfer catalysts, but these reaction properties of amides cannot be compared with those of amines because of the higher acidity of the amides.

Diethyl carbonate in general reacts with amines to give carbamic acid esters (Houben-Weyl, Methods of Organic Chemistry, Volume E 4, page 159; Ullmann's Encyclopaedia of Industrial Chemistry, 4th edition, Volume 14, page 591; DE-B-2160111), and U.S. Pat. No. 4,550,188 discloses ethylation only as a side-reaction.

Only in a few cases ethylations occur as the main reaction in the reactions of aromatic amines with diethyl carbonate. DE-A-2618033 also describes, in addition to the reactions of various aniline derivatives with dimethyl carbonate, the reaction of p-phenylenediamine and p-toluidine. Two monoarylamines activated by electron-donating substituents on the ring, with diethyl carbonate in which mixtures of products mono- and bis-ethylated on the nitrogen are formed. The gas phase reaction of aniline, a relatively highly volatile aromatic amine, with diethyl carbonate in the presence of a catalyst comprising polyethylene glycol and potassium carbonate gives a mixture of 56.5% of N-ethylaniline, 19.7% of N-ethoxycarbonyl-N-ethylaniline and 24.4% of aniline (*Journal of Organic Chemistry*, Volume 52, page 1300, 1987). It clearly observed that a high proportion of starting material remains un-reacted. This method cannot therefore be applied to amines of low volatility. Alkylation of aromatic amines by means, of dialkyl carbonates in the presence of organic iodides as catalysts is mentioned in German Patent Specification DE-C-3007196. However, because of the addition of organic iodides, industrial realization of this process would again necessitate expensive purification of waste air. Further, with aqueous working-up, it would lead to a content of organic halogen compounds in the wastewater. Furthermore, only reactions with dimethyl carbonate, from which mixtures of N-methyl- and N,N-di-methyl-anilines are obtained, are disclosed. There are no indications that diethyl carbonate gives results similar to those with dimethyl carbonate, which has a substantially better alkylating action. The markedly different alkylation capacity of methyl and ethyl groups in carbonic acid esters can also be seen from EP-B-104601 which also discloses the use, in addition to the use of dimethyl carbonate, of the mixed carbonic acid esters with a methyl group and a higher alkyl group, for example, and preferably, an ethyl group, for N-methylation of bis(2,4,6-tribromophenyl)amine to give the desired N,N-bis(2,4,6-tribromophenyl)methylamine. Alkylation proceeding along-side the methylation, in particular ethylation, which would indicate comparable reaction properties of the methyl and ethyl group in this type of reaction of N-alkylation of a diarylamine, is not referred. However, even with dimethyl carbonate, the reaction is also not complete, so that the separation of reactant and product becomes necessary.

N-Ethyl carbazole is used in the synthesis of useful dyes and pigments. It is used as one of the main constituents in the synthesis of Pigment Violet-23 (PV-23) and its demand in printing ink, plastic and paint industry is increasing rapidly. With rising prices of carbazole and intense market competition, it is found essential to substantially reduce the manufacturing cost of PV-23 so as to be very competitive in the growing pigment market. This lead us to study various steps involved in the application of Bischler synthesis for the preparation of carbazole derivative cheaply so as to make our product more competitive.

Synthesis of carbazole and tetrahydro carbazole by Bischler reaction is very well known in the prior art. Application of Bischler synthesis for the preparation of tetrahydrocarbazoles is first mentioned in DE 374098 (1923). The German patent discloses synthesis of tetrahydrocarbazoles by condensing 1,2-halocyclohexanones with primary or secondary aromatic amines. Furthermore, DE947068 discloses synthesis of tetrahydrocarbazoles by reaction of 2-halogen cyclohexanones with primary or secondary aromatic amines having at least one unsubstituted o-position in the atmosphere of an inert gases free from molecular oxygen.

The availability of wide variety of aromatic amines and the ease with which 2-chloro cyclohexanones reacts with it makes the Bischler synthesis a very attractive method for the preparation of tetrahydrocarbazoles.

Rogers and Corson, *J. Am. Soc.*, 69, 2910, 1947, describes one-step synthesis of tetrahydrocarbazole from cyclohexanone and phenyl hydrazine. This is aromatized by heating with chloranil in xylene (Barclay and Campbell, J. Chem. Soc. 530, 1945).

K. Darrell Berlin, Peter E. Clark, Jack Schroeder and Darrell Hopper, *Proc. of the Okala. Acad. of sci.* for 1966, pg 215-220, reports synthesis of 3-tert-butyl-1,2,3,4-tetrahydrocarbazole with 81% yield in acetic acid after 2.5 hours reflux. When the reaction is run for 5 hours, yield dropped down to 78.8%.

E. Campaigne and R. D. Lake, *Journal of Organic Chemistry* (1959), 24, 478-87, describes synthesis of 2-N-ethyl anilino cyclohexanone from reaction of N-ethylaniline (0.20 M) with 2-chloro cyclohexanone (0.20 M), quinoline (0.02 M), sodium carbonate (0.30 M) and 150 ml of methylcellosolve (solvent) which gives 42% yield after 45 minutes reflux. The crude tetrahydrocarbazole is purified by converting it to picrates or purified by passing through alumina column which is then dehydrogenated using 30% Pd-carbon catalyst (0.25-0.4 g of 30% Pd—C catalyst per g of N-ethyl tetrahydrocarbazole with 10 ml/g Xylene after 12 hour, reflux.

The processes disclosed in the prior art for the synthesis of N-ethyl tetrahydrocarbazole require solvent or dehydrating agent. Further, the yield and purity of the alkyl carbazole synthesized from tetrahydrocarbazole by the processes disclosed in the prior art are very low. Accordingly, it is desirable to develop a process for the preparation of N-ethyl tetrahydrocarbazole in higher yield and purity from 2-chloro cyclohexanone and N-ethyl aniline in absence of any solvent or dehydrating agent.

OBJECTS OF THE INVENTION

It is an object of the present invention to prepare N-alkyl tetrahydrocarbazole.

It is another object of the present invention to provide a process for the preparation of N-alkyl carbazole.

It is still another object of the present invention to provide a process which provide highly pure product in high amount.

It is a further object, of the present invention to provide a process which is simple, safe, convenient, easy to operate on commercial scale and cost-effective.

SUMMARY OF THE INVENTION

In accordance with the present invention there is provided a process for the preparation of N-alkyl carbazole; said process comprising the following steps:
a. chlorinating cyclohexanone to form 2-chlorocyclohexanone;
b. reacting 2-chlorocylohexanone with N-ethyl aniline to form 2-(N-ethyl anilino) cyclohexanone;
c. cyclizing 2-(N-ethyl anilino) cyclohexanone by refluxing with simultaneous water removal to obtain 9-ethyl-tetrahydrocarbazole;
d. treating 9-ethyl-tetrahydrocarbazole with concentrated hydrochloric acid followed by water wash for removing N-ethyl aniline;
e. dehydrogenating 9-ethyl-tetrahydrocarbazole by heating 9-ethyl-tetrahydrocarbazole in a solvent, in presence of a catalyst to obtain N-alkyl carbazole.

In accordance with another embodiment of the present invention, the process further comprising the method step of washing N-alkyl carbazole with a solvent followed by filtration to remove the catalyst.

Typically, the catalyst is re-usable.

Typically, the catalyst is selected from the group consisting of palladium on carbon, Raney nickel and platinum.

Preferably, the catalyst is palladium on carbon.

Typically, the concentration of the catalyst used is about 5 to 30%.

Typically, the proportion of catalyst used is in the range of about 1 to about 10% of the mass of the 9-ethyl-tetrahydrocarbazole.

Preferably, the proportion of catalyst used is about 5% of the mass of the 9-ethyl-tetrahydrocarbazole.

Typically, the dehydrogenation is carried out at a temperature in the range of about 160 to about 250° C.

Preferably, the dehydrogenation is carried out at a temperature of about 200° C.

Typically, the solvent is at least one selected from the group consisting of o-xylene, diphenyl ether, 1,2,4-trimethyl benzene, isopropyl benzene, cyclohexyl propionate and 1,2,4,5 tetramethyl bezene.

Typically, the reaction is carried out for a period of about 8 to 22 hours.

Typically, the conversion of tetrahydro-carbazole to N-alkyl carbazole is greater than 98%.

DETAILED DESCRIPTION OF THE INVENTION

In accordance with the present invention there is provided a process for the preparation of N-alkyl carbazole.

Inventors of the present invention carefully studied the various steps involved in the application of the Bischler synthesis for the preparation of carbazoles and its derivatives. It is found best to prepare first the arylaminocyclohexanones, cyclize these to the desired tetrahydrocarbazoles under controlled conditions, and then dehydrogenate the product with appropriate dehydrogenation catalysts to obtain the desired carbazole derivatives in high yield and purity.

The process for the preparation of N-alkyl carbazole in accordance with the present invention comprising the following steps:

First step is chlorinating cyclohexanone to form 2-chlorocyclohexanone. The obtained 2-chlorocylohexanone is then reacted with N-ethyl aniline to form 2-(N-ethyl anilino)cyclohexanone which is further heated to reflux with simultaneous water removal to complete the cyclization which results in formation of 9-ethyl-tetrahydrocarbazole. Excess of N-ethyl aniline is then removed by treatment with conc. hydrochloric acid and water wash. The obtained organic layer is then washed to make acid free and concentrated to get 9-ethyl tetrahydrocarbazole as a viscous liquid. The crude product is taken for next step without further treatment. N-ethyl aniline is regenerated from aqueous hydrochloride solution by basification.

The next step is dehydrogenating the 9-ethyl tetrahydrocarbazole in a solvent, in presence of a metal catalyst.

The metal catalyst used for dehydrogenation is selected from the group consisting of palladium on carbon, Raney nickel and platinum.

According to the most preferred embodiment, N-ethyl carbazole is synthesized by dehydrogenation of 9-ethyl tetrahydrocarbazole in the presence of nitrogen atmosphere by heating 9-ethyl tetrahydrocarbazole with Pd-Carbon catalyst in a solvent selected from the group consisting of o-xylene, diphenyl ether, 1,2,4-trimethyl benzene, isopropyl benzene, cyclohexyl propionate and 1,2,4,5 tetramethyl bezene.

The concentration of the catalyst used for dehydrogenation is about 5 to 30% and the proportion of the catalyst used is about 1 to about 10% of the mass of the 9-ethyl tetrahydrocarbazole. Preferably, proportion of the catalyst used is about 5% of the mass of the 9-ethyl tetrahydrocarbazole.

The dehydrogenation step is carried out at a temperature in the range of about 160 to about 250° C. for a period of about 8 to about 22 hours. Preferably the dehydrogenation step is carried out at a temperature of about 200° C.

The conversion of tetrahydrocarbazole obtained by the process of present invention is >98%. The yield of N-ethyl carbazole on the converted material is nearly quantitative. It is not necessary to take the dehydrogenation to completion. The unreacted tetrahydrocarbazole can be removed by crystallization of the crude N-ethyl carbazole in a suitable solvent and the filtrate containing N-ethyl tetrahydrocarbazole can be recycled for next batch of dehydrogenation. The ease of repeated recycle (at least three time) of catalyst in the next dehydrogenation batch indicates that the catalyst do not get poisoned during dehydrogenation in spite of using crude N-ethyl tetrahydrocarbazole.

In accordance with one of the embodiments of the present invention, Raney nickel, in an amount of about 1% w/w is used as a catalyst for dehydrogenation of 9-ethyl tetrahydrocarbazole. The conversion of tetrahydrocarbazole at 250° C. over a period of about 15 hours was found to be only 16%.

In accordance with another embodiment of the present invention the dehydrogenation of 9-ethyl tetrahydrocarbazole is carried in diphenyl ether instead of o-xylene at 200° C. Reaction was completed in 8 hours with 98% conversion.

The invention will now be described with respect to the following examples which do not limit the invention in any way and only exemplify the invention.

Example 1

Preparation of 2-Chlorocyclohexanone 490 g of cyclohexanone was added to water (1250 ml) to obtain a mixture. The mixture was stirred vigorously at 20° C. in a 4 lit. capacity integrated reactor provided with mechanical stirrer, dip tube inlet for chlorine introduction, thermowell and a reflux condenser. Chlorine was then introduced at the rate of 71 g/hour for 4 hours with vigorous stirring. The reaction mixture was allowed to settle. Bottom organic layer was separated from the aqueous layer and neutralized with $Na_2CO_3$ solution which was then settled to get oily layer. The combined oily layer gave 436 g of 2-chlorocyclohexanone, 102 g cyclohexanone and 54 g of dichloro. Yield of 2-chloro cyclohexanone: 82% with >98% GC purity.

Example 2

Preparation of 9-ethyl-1,2,3,4-tetrahydrocarbazole 266.2 g of N-ethyl aniline was taken in a reactor provided with a mechanical stirrer, thermowell and a double coil condenser with ice water circulation above a dean and stark apparatus. To this 132.5 g of 2-chloro cyclohexanone was added over a period of 1 hour to obtain a reaction mass which was heated to 100° C. and stirred for 2 hours. The reaction mass was further heated to 150-160° C. when exotherm was observed and stirred for 2 hours. Water generated in the reaction was removed by applying vacuum from the top of the condenser (provided with ice water circulation) and maintained till theoretical water was collected in the side arm of dean and stark apparatus. Excess N-ethyl aniline was precipitated by adding conc. HCl and water wash. The obtained organic layer was washed acid free and concentrated under reduced pressure to get 178.2 g of viscous liquid (89% yield) with GC purity 98.4%. The mass spectra matches with molecular ion peak (199).

N-ethyl aniline was regenerated from aqueous hydrochloride solution by basification, extraction and distillation. N-Ethyl aniline recovered was 113.2 g.

Comparative Example 132.5 g of 2-chloro-cyclohexanone was added to 123.42 g of N-ethyl aniline, 500 ml of methyl cellosolve, 127 g of dry sodium carbonate and 7.9 g of pyridine at 30-40° C. over a period of 1 hour. Reaction mass was heated to 100° C. and stirred for 2 hours. Reaction temperature was further raised to 130° C. and held at this temperature till no more water get distilled. Reaction mass was then worked up to get 48.2 g of crude 9-ethyl-tetrahydrocarbazole of 96.3% GC purity.

Example 3

266.2 g N-ethyl aniline was charged in a reactor along with 200 ml o-xylene. To this 132.5 g of 2-chloro-cyclohexanone was added over a period of 2 hours to obtain a clear solution which was then heated to 100° C. and stirred for 2 hours with water removal. The contents were further heated to 150-160° C. with simultaneous water removal by applying mild vacuum. The reaction mass was worked up as above to get 136 g crude 9-ethyl tetrahydrocarbazole with 96.8% GC purity.

Example 4

Dehydrogenation of Tetrahydrocarbazole
[Preparation of N-ethyl carbazole]

70 g of 9-ethyl-1,2,3,4-tetrahydrocarbazole (98.6%) was charged in a reactor along with 35 ml o-xylene. 1.4 g. of 5% Pd-Carbon catalyst was added to the above mass and the contents were heated to 200° C. under a slow current of nitrogen after partial distillation of solvent and maintained for 10 hours. Reaction progress was checked by gas layer chromatography by removing samples at various time intervals. After maintenance of 10 hours at 200° C., 99% conversion of tetrahydrocarbazole was achieved. Reaction mixture was cooled to room temperature by adding more xylene. The reaction mass was then filtered to remove catalyst and washed with little o-xylene. Xylene layer on concentration under reduced pressure gave 67.8 g solids and 98.6% GC purity. The filtered catalyst is reused for next batch of dehydrogenation.

N-ethyl carbazole was crystallized from a mixture of toluene and hexane after treatment with activated carbon to get 99.9% pure crop. Elemental analysis and NMR spectra support the structure of N-ethyl carbazole.

Elemental analysis is as follows:
C=86.215%; H=6.40%; N=7.067% (Theoretical C=86.22%; H=6.73%; N=7.18%).

Example 5

Recycle of Catalyst in Dehydrogenation of Tetrahydrocarbazole 70 g of 9-ethyl-1,2,3,4-tetrahydrocarbazole was charged along with 3.5 g of filtered wet catalyst obtained from above batch (2 wt % on dry basis) and 35 ml o-xylene. The content were heated under a slow current of nitrogen to achieve 200° C. liquid temperature and maintained for 15 hour to get GC conversion of 82% 9-ethyl carbazole and 17% 9-ethyl-tetrahydrocarbazole. Further, 0.3 g fresh 5%-Pd-carbon (50% moisture) was added at this stage and the reaction was maintained at 200° C. for further 6 hours to get 99% conversion. The reaction mass was then filtered to remove the catalyst and the filtrate was concentrated under reduced pressure to get 67.9 g crude product with GC purity of 98.4%. Filtered catalyst was further recycled three times by adding fresh 5% Pd-c catalyst, 10% of initial catalyst loading to achieve higher conversion.

Technical Advance

In accordance with the present invention there is provided a process for the preparation of N-ethyl carbazole by dehydrogenation of N-ethyl tetrahydrocarbazole in the presence of a metal catalyst. The catalyst used can be isolated and reused for further dehydrogenation step.

Further, the present invention relates to preparation of N-ethyl tetrahydrocarbazole in higher yield and purity from 2-chloro cyclohexanone and N-ethyl aniline in absence of any solvent or dehydrating agent.

Still further, the present process involves use of crude N-ethyl tetrahydrocarbazole for dehydrogenation without any purification to get high yield of N-ethyl carbazole in a form, which is readily purified or can be used as such for the next step.

The invention claimed is:

1. A process for the preparation of N-alkyl carbazole; said process comprising the following steps:
   a. chlorinating cyclohexanone to form 2-chlorocyclohexanone;
   b. reacting 2-chlorocylohexanone with N-alkyl aniline to form 2-(N-alkyl anilino) cyclohexanone in the absence of dehydrating agent and solvent;
   c. cyclizing 2-(N-alkyl anilino)cyclohexanone by refluxing with simultaneous water removal to obtain 9-alkyl-tetrahydrocarbazole in the absence of dehydrating agent and solvent;
   d. treating 9-alkyl-tetrahydrocarbazole with concentrated hydrochloric acid followed by water wash for removing N-alkyl aniline; and
   e. dehydrogenating 9-alkyl-tetrahydrocarbazole by heating 9-alkyl-tetrahydrocarbazole in a solvent, in presence of a catalyst to obtain N-alkyl carbazole.

2. The process as claimed in claim 1, further comprising a step of washing N-alkyl carbazole with a solvent followed by filtration to remove the catalyst and recycle the catalyst.

3. The process as claimed in claim 1, wherein the catalyst is selected from the group consisting of palladium on carbon, Raney nickel and platinum.

4. The process as claimed in claim 1, wherein the catalyst is palladium on carbon.

5. The process as claimed in claim 1, wherein the concentration of the catalyst used is about 5 to 30%.

6. The process as claimed in claim 1, wherein the proportion of catalyst used is in the range of about 1 to about 10% of the mass of the 9-alkyl-tetrahydrocarbazole.

7. The process as claimed in claim 1, wherein the proportion of catalyst used is about 5% of the mass of the 9-alkyl-tetrahydrocarbazole.

8. The process as claimed in claim 1, wherein the dehydrogenation is carried out at a temperature in the range of about 160 to about 250° C.

9. The process as claimed in claim 1, wherein the dehydrogenation is carried out at a temperature of about 200° C.

10. The process as claimed in claim 1, wherein the solvent is at least one selected from the group consisting of o-xylene, diphenyl ether, 1,2,4-trimethyl benzene, isopropyl benzene, cyclohexyl propionate and 1,2,4,5 tetramethyl benzene.

11. The process as claimed in claim 1, wherein the reaction is carried out for a period of about 8 to 22 hours.

12. The process as claimed in claim 1, wherein the conversion of N-alkyl-tetrahydro-carbazole to N-alkyl carbazole is greater than 98%.

13. The process as claimed in claim 1, wherein the N-alkyl carbazole is N-ethyl carbazole.

14. The process as claimed in claim 1, wherein the N-alkyl aniline is N-ethyl aniline.

* * * * *